(12) United States Patent
Shepard et al.

(10) Patent No.: US 7,323,011 B2
(45) Date of Patent: Jan. 29, 2008

(54) CORTICAL AND CANCELLOUS ALLOGRAFT CERVICAL FUSION BLOCK

(75) Inventors: Yolanda Denise Shepard, Parlin, NJ (US); Manuel A. Olivos Sanchez, Harrison, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 295 days.

(21) Appl. No.: 10/273,177

(22) Filed: Oct. 18, 2002

(65) Prior Publication Data
US 2004/0078078 A1   Apr. 22, 2004

(51) Int. Cl.
*A61F 2/44* (2006.01)
(52) U.S. Cl. .................................. 623/17.11
(58) Field of Classification Search ............. 623/16.11, 623/17.11–17.16, 23.51, 23.75
See application file for complete search history.

(56) References Cited

U.S. PATENT DOCUMENTS

| | | | |
|---|---|---|---|
| 4,950,296 A | | 8/1990 | McIntyre |
| 5,766,618 A | * | 6/1998 | Laurencin et al. .......... 424/426 |
| 5,972,368 A | | 10/1999 | McKay |
| 6,037,519 A | * | 3/2000 | McKay ........................ 623/16 |
| 6,136,029 A | * | 10/2000 | Johnson et al. ............... 623/16 |
| 6,187,329 B1 | * | 2/2001 | Agrawal et al. ............. 424/426 |
| 6,200,347 B1 | * | 3/2001 | Anderson et al. ......... 623/16.11 |
| 6,294,187 B1 | | 9/2001 | Boyce et al. |
| 6,379,385 B1 | | 4/2002 | Kalas et al. |
| 6,398,811 B1 | * | 6/2002 | McKay .................... 623/17.16 |
| 6,458,158 B1 | * | 10/2002 | Anderson et al. ......... 623/16.11 |
| 6,652,593 B2 | * | 11/2003 | Boyer et al. ............. 623/23.63 |
| 2001/0041941 A1 | * | 11/2001 | Boyer, II et al. ......... 623/23.52 |
| 2002/0029084 A1 | | 3/2002 | Paul et al. |
| 2003/0028197 A1 | * | 2/2003 | Hanson et al. ................ 606/99 |
| 2003/0036800 A1 | * | 2/2003 | Meredith ................. 623/23.63 |
| 2003/0105528 A1 | * | 6/2003 | Shimp et al. ............. 623/17.16 |

FOREIGN PATENT DOCUMENTS

WO   WO 02/07654 A2   1/2002
WO   WO 02/24122 A2   3/2002

OTHER PUBLICATIONS

F. Albee, *Bone Graft Survery in Disease, Injury and Deformity*, p. 22 (1940).

* cited by examiner

*Primary Examiner*—Anuradha Ramana
(74) *Attorney, Agent, or Firm*—John S. Hale; Gipple & Hale

(57) ABSTRACT

A sterile composite bone graft for use in implants comprising a T shaped cortical bone load bearing member mated to a cancellous member. The crosspiece of the T defines an inner planar surface and dove tail shaped mating member extends outward from the inner planar surface. The allograft cancellous bone member defines tapered side walls on the exterior surface of the body, a flat proximal end surface and a flat distal end surface. A dove tail shaped recess with the narrowest portion exiting the flat proximal end surface is cut into the interior of the cancellous member body. The dove tail shaped member and dove tail shaped recess are mated together to hold both component members together. Pins are mounted in both members to provide additional stability.

47 Claims, 5 Drawing Sheets

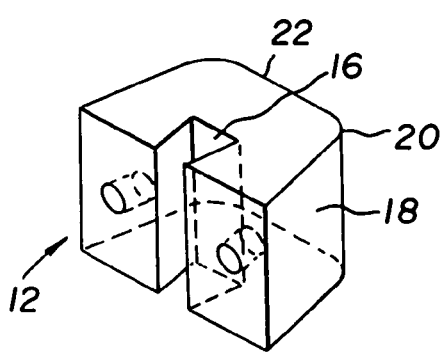
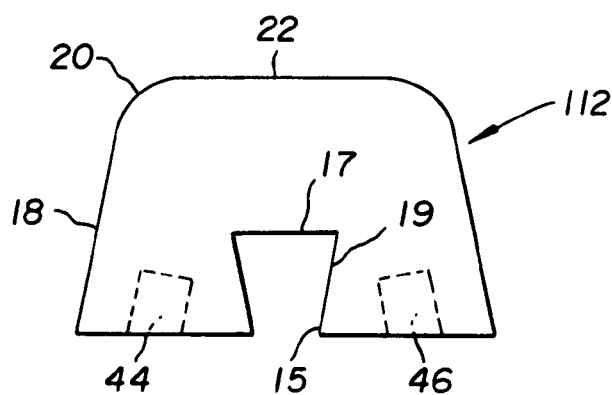
Fig. 3  Fig. 4
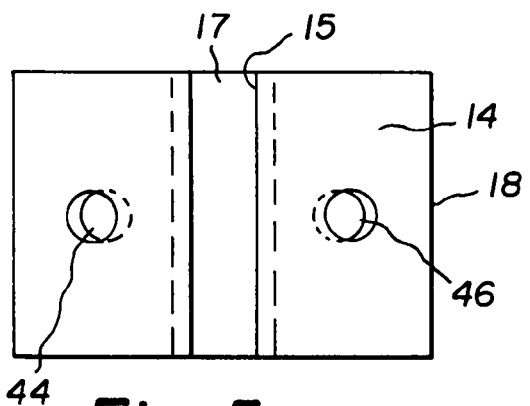
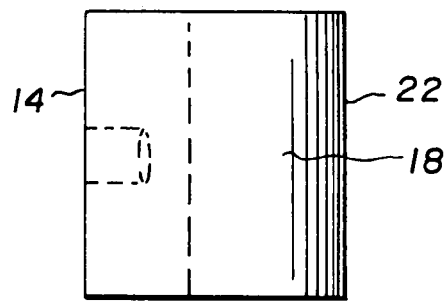
Fig. 5  Fig. 6
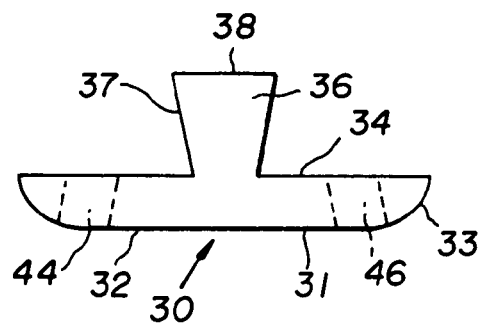
Fig. 7
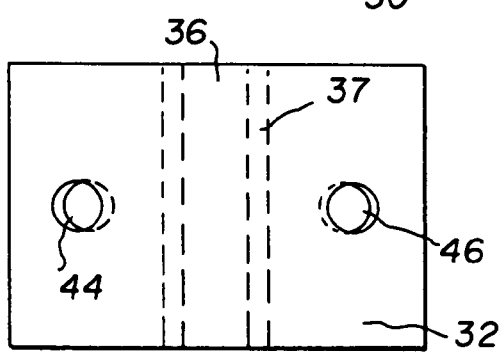
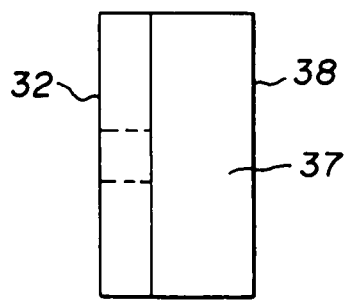
Fig. 8  Fig. 9

CORTICAL AND CANCELLOUS ALLOGRAFT CERVICAL FUSION BLOCK

RELATED APPLICATION

There are no related applications.

FIELD OF INVENTION

The present invention is generally directed toward a surgical implant product and more specifically is a shaped allograft cortical cancellous bone block implant for the fusion of vertebral bones which is introduced between two vertebral bones to be fused.

BACKGROUND OF THE INVENTION

The use of substitute bone tissue dates back around 1800. Since that time research efforts have been undertaken toward the use of materials which are close to bone in composition to facilitate integration of bone grafts. Developments have taken place in the use of grafts to use materials such as corals, hydroxyapatites, ceramics or synthetic materials such as biodegradable polymer materials. Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Human allograft tissue is widely used in orthopaedic, neuro-, maxillofacial, podiatric and dental surgery. The tissue is valuable because it is biocompatible, strong, biointegrates in time with the recipient patient's tissue and can be shaped either by the surgeon to fit the specific surgical defect or shaped commercially in a manufacturing environment. Contrasted to most synthetic absorbable or nonabsorbable polymers or metals, allograft tissue integrates with the surrounding tissues.

Allograft bone is a logical substitute for autologous bone. It is readily available and precludes the surgical complications and patient morbidity associated with obtaining autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

Alograft bone occurs in two basic forms; cancellous and cortical. The cancellous bone includes void areas with the collagen fiber component contributing in part to torsional and tensile strength. The less dense cancellous bone provides an excellent matrix for rapid bone regeneration and repair.

Many devices of varying shapes and forms are fabricated from allograft cortical tissue by machining. Surgical implants such as pins, rods, screws, anchors, plates, intervertebral spacers and the like have been made and used successfully in human surgery. These pre-engineered shapes are used by the surgeon in surgery to restore defects in bone to the bone's original anatomical shape.

Injury or disease processes to the head, neck, or shoulders can cause abnormal forces to be applied on the cervical vertebra. Arthritis, motion induced "whiplash", or other trauma create this malfunction. This situation is often treated surgically by a procedure intended to fuse the two adjacent cervical or spinal vertebrae to each other. Such fusion relieves the pressure the partially displaced vertebrae place on the adjacent spinal nerves.

Many surgical devices have been developed and used successfully to immobilize and fuse the misaligned vertebrae. Metal plates screwed into the adjacent vertebrae work well, but after some time post-operatively, the stress rise occurring at the screw position causes erosion of the bone and resultant slipping. This has been improved by placing load-bearing spacers between the two (or more) misaligned vertebrae. The spacer is both load-bearing and of a material which will induce, or at least support, fusion between the vertebrae.

Removal of damaged or diseased discs, restoration of disc space height and fusion of adjacent vertebrae to treat chronic back pain and other ailments are known medical techniques. Implants such as intervertebral spacers are often implanted in the disc space engaging the vertebrae to maintain or reestablish disc space height after removal of all or a portion of the disc. The spacers are formed of a variety of both resorbable and non-resorbable materials, including, for example, titanium, surgical steel, polymers, composites and bone. It is currently considered desirable to promote fusion between the vertebral bodies that are adjacent to the damaged or diseased discs. Typically, an osteogenic material is combined with a spacer and inserted in the disc space to facilitate and promote bone growth. While the selection of the implant configuration and composition can depend upon a variety of considerations, it is often desirable to select a resorbable material that does not shield the bone ingrowth. Bone and bone-derived components can provide suitable material to prepare the implants. However, bone material and in particular cortical bone acceptable for use in implants is a scarce resource, being derived from limited number human tissue donor resources.

Suitable bone or bone-derived material for use in implants, in general, is almost exclusively obtained from allograft and xenograft sources, both of which come from a limited supply. Since intervertebral spacers must withstand the compressive loads exerted by the spine, these implants are often cortical bone which has the mechanical strength suitable for use in any region of the spine. Cortical spacers are often shaped from cortical long bones, which are primarily found in the lower limbs and include, for example, femur, fibula, and the tibia bones. However, these long bones make up only a fraction of the available bone source. Cancellous bone, because of its superior osteoinductive properties, would be desirable to sue in the spinal implant. However, the lower mechanical strength of cancellous bone prohibits its use in many surgical applications. Thus, sources of bone suitable for structural intervertebral spacers are extremely limited. The scarcity of desired donor bone makes it difficult to provide implants having the desired size and configuration for implantation between vertebrae, which can require relatively large implants. It is further anticipated that as the population ages there will be an increased need for correction for spinal deformities and a concomitant increase in the demand for bone-derived components. Therefore, these structural bone portions must be conserved and used efficiently to provide implants. The scarcity of suitable bone material has also hindered efforts to design and manufacture varying configurations of suitable implants for arthodesis of the spine. Further, various implant configurations have not been physiologically possible to obtain given the structural and geometrical constraints of available donor bone.

One known treatment for fusing two vertebrae is the insertion of a suitably shaped dowel into a prepared cylindrical cavity which reaches the two vertebrae to be fused. The dowel used is preshaped bone or allograft bone.

A number of allograft bone spacers have been used in surgery as spacers. They are commonly called the ACF spacer constructed as a cortical bone cross section, shaped like a washer with teeth to discourage graft explusion and an axial center hole; a VG3 cervical spacer constructed with two ramp shaped cortical plates held together with cortical pins, the top and bottom surfaces being ridged to discourage graft expulsion; an ICW spacer constructed with an elongated C spaced cortical portion with a cancellous inside to allow rapid ingrowth (slice of iliac crest) and a SBS spacer constructed with a single piece cortical member with serrated top and bottom surfaces and an axial center hole.

The ICW (iliac crest wedge) has been used for a long time for cervical spine fusion and has a total load bearing force around 4500 Newtons. Testing has noted that cervical vertebrae fail in compression at about 2000 Newtons. The ICW spacer suffers from high unit variability because of its natural, anatomic variations.

U.S. Pat. No. 5,972,368 issued on Oct. 26, 1999 discloses the use of cortical constructs (e.g. a cortical dowel for spinal fusion) which are cleaned to remove all of the cellular material, fat, free collagen and non-collagenous protein leaving structural or bound collagen which is associated with bone mineral to form the trabecular struts of bone. The shaped bone is processed to remove associated non-collagenous bone proteins while maintaining native bound collagen materials and naturally associated bone minerals. The surface of a machined cortical bone is characterized by a wide variety of openings resulting from exposure by the machining process of the Haversian canals present throughout cortical bone. These canals serve to transport fluids throughout the bone to facilitate the biochemical processes that occur at variable angles and depths within the bone.

An attempt to solve the increasing bone supply problems using a combined cortical and cancellous bone block is shown in U.S. Pat. No. 4,950,296 issued Aug. 21, 1990 which uses a cubically configured cortical shell defining a through going internal cavity and a cancellous plug fitted into the cavity so that the end surfaces of the cancellous plug are exposed. Another reference, WIPO Patent Publication Number WO 02/24122 A2, published Mar. 28, 2002 owned by SDGI Holdings Inc. show various intervertebral spacers formed of cortical and cancellous bone composites such as sandwiches, with intersecting ribs and rods.

U.S. Pat. No. 6,294,187 issued Sep. 25, 2001 is directed toward an shaped osteimplant of compressed bone particles. The shaped implant is disc shaped and has a number of holes drilled therein for macroporosity and the holes can be filled with an osteogenic putty material.

Conversely, WIPO Patent Publication Number WO 02/07654 A2, published Jan. 31, 2002 discloses intervertebral spacers formed of dense cancellous human or animal bone. In one embodiment, a cortical rod or cortical rods are placed in bores cut through a cancellous bone block to provide load bearing strength with the ends of the rods being exposed on both sides of the cancellous bone block. Another embodiment shows a C shaped cortical block with a cancellous plug inserted into the recess of the C to form a rectangular spacer. A pin is inserted through a bore cut through the legs of the C block and through the cancellous plug to keep the cancellous plug positioned with the recess of the cortical component. U.S. Pat. No. 6,379,385 issued Apr. 30, 2002 also discloses the use of a spongy block having a plurality of cortical rods mounted in through going bores cut through the bone block. In another embodiment, a X-shaped cortical support member is mounted therein to provide structured strength to the composite implant.

It is also known to mate various bone components together to form a single implant. In this regard, see, Albee, *Bone Graft Surgery in Disease, Injury and Deformity*, (1940), pp. 30, which uses a tongue in groove and dove tail to hold separate pieces of bone together for implant use, and U.S. Publication No. US2002/0029084 A1, published Mar. 7, 2002, which shows a three component implant with a center core surrounded by two outer semicircular portions. The outer portions have alternative dove tail joints on adjacent bone portions to secure the outer portions together forming a dowel shaped bone implant.

Consequently, there is a need for an implant which should have with a load bearing compressive strength of 1000 to 5000 Newtons with a compressive load to be a minimum of 3000 Newtons as a safety factor. There is also a need to have a portion of cancellous bone immediately adjacent to the load bearing cortical zone to permit rapid ingrowth of a patient's own new bone with the cancellous bone forming the major part of the implant.

SUMMARY OF THE INVENTION

The composite allograft cervical fusion block is directed toward a two piece, mated bone fusion block or spacer constructed with one component member of load bearing material preferably cortical bone and the other component member made of cancellous bone for use in orthopedic surgical procedures. The cortical bone member defines a dove tail shaped projection extending from its outer surface with the cancellous component member having a dove tail recess cut therein to receive the dove tail projection of the cortical member. A plurality of bores are cut through the cortical bone member and into the cancellous member to hold pins which are angularly inserted into the bores along opposite sides of the dove tail projection and recess and through the head of the cortical member to limit axial and lateral movement.

Additional embodiments include the use of a single throughgoing pin, a single transverse throughgoing pin, multiple dove tails, a bulbous projection substituted for the dove tail and opposing load bearing members.

It is an object of the invention to use a bone block geometry to provide a composite bone block of cancellous and cortical bone components having performance characteristics that meet or exceed conventional spinal fusion requirements.

It is another object of the invention to utilize a shaped cortical cancellous bone implant block which provides the mechanical strength characteristics that can withstand compression forces and provide overall strength and durability to the structure.

It is still another object of the invention to provide a spinal fusion implant which uses a load bearing component member to take up the high forces which can arise between two vertebral bodies and a relatively porous cancellous component member to accelerate the healing process.

It is yet another object of the invention to provide a pre-machined shaped allograft bone structure which can effectively promote new bone growth and accelerate healing.

It is also an object of the invention to create a sterile bone fusion implant, which is sterile and which can be easily handled by the physician during surgery which eliminates or significantly reduces the physician from having to carve or modify the respective bone blocks.

These and other objects, advantages, and novel features of the present invention will become apparent when considered with the teachings contained in the detailed disclosure. This disclosure, along with the accompanying drawings and description, constitutes a part of this specification and illustrates embodiments of the invention which serve to explain the principles of the invention.

BRIEF DESCRIPTION OF THE DRAWINGS

FIG. 3 is a perspective view in phantom of the cancellous component of FIG. 1;

FIG. 4 is an enlarged top plan view of the cancellous component of FIG. 3 showing the bores in phantom;

FIG. 5 is an enlarged front right side elevational view of the cancellous component of FIG. 3;

FIG. 6 is a right side elevational view of the cancellous component of FIG. 3;

FIG. 7 is a top plan of the cortical component of FIG. 1;

FIG. 8 is a front elevational view of the cortical component of FIG. 7 showing the dove tail in phantom;

FIG. 9 is a side elevational view of the cortical component of FIG. 7;

DETAILED DESCRIPTION OF THE INVENTION

Figure 1:
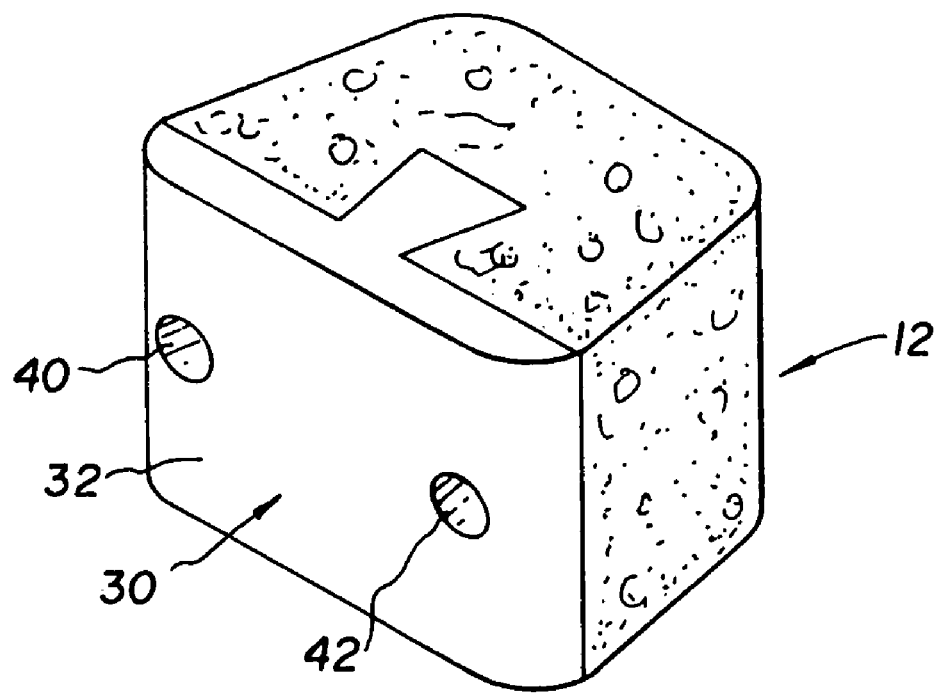
FIG. 1 is a perspective view of the inventive composite cortical and cancellous component bone implant.
Figure 2:
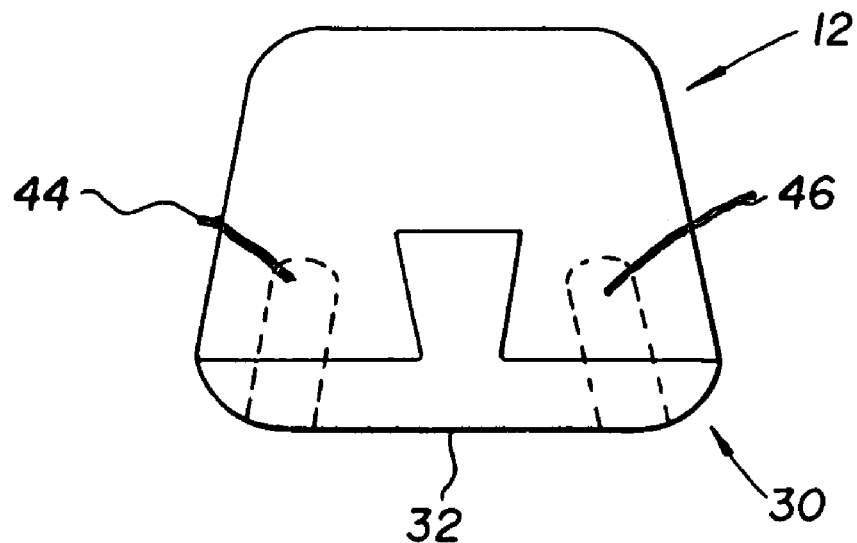
FIG. 2 is a top plan view of the implant of FIG. 1.

The preferred embodiment and best mode of the present invention is shown in FIGS. 1 through 9. The composite bone implant block 10 is shown in FIG. 1 in accordance with the present invention.

The composite cortical cancellous bone block body or intervertebral spacer 10 is preferably constructed with a first component member 12 of denser cancellous bone taken from donors age 45 or less cut into a truncated triangle shape. This component accounts for a large portion of the graft and provides a large area for bone fusion to occur. The component member body has a flat planar front end surface 14 and is provided with a dove tail shaped recess 16 cut therein into the interior of the cancellous component body. The dove tail shaped recess 16 extends from the access port or opening 15 to the base wall 17 forming the rear of the recess. The access entrance opening 15 is preferably about twice as wide as the base 17 of the recess and the side walls 19 of the recess are angled from 76° to 95° outward from the entrance opening 15. The cancellous bone is harvested from a bone such as a tibia, humerus, patella, calcaneus or femur. The side walls 18 of the cancellous member 12 are tapered or angled from 100° to 110°, preferably at 101° with a tapered distal side section 20 running into a planar rear wall surface 22. The cancellous member 12 when implanted in the patient's body encourages tissue, vascularation and deposition of new bone.

The cortical cancellous bone block 10 has a T shaped cortical component member 30 with a cross piece 31 having planar outer surface 32 and two tapered or curved side sections 33 which lead to an inner flat planar surface 34. A dove tail shaped projection 36 which has approximately the same dimensions as dove tail recess 16 cut into the cancellous member extends outward from the planar surface 34. The projection or mating member 36 has angled side walls 37 extending outward at an angle ranging from 70° to 75° to mate with the recess 16. The end 38 of the dove tail projection 36 is planar. The cortical member 30 has superior wall strength for support between load bearing body structures such as vertebrae. While it is noted that wall surfaces 14 and 34 are flat, these surfaces can be provided with any kind of complementary construction.

When the composite assembly is lyophilized, the pieces shrink with the cortical bone shrinking about 3% and the cancellous bone shrinking a greater amount ranging from 4% to 8%. Thus, the dove tail projection 36 will loosely fit into the dove tail recess 16 to hold the two components together. The cortical member 30 has superior wall strength for support between load bearing body structures such as vertebrae and has a compressive load ranging from 2000 to 5000 Newtons, preferably in excess of 3000 Newtons. The composite bone block body 10 height can range from 8-12 mm preferably 10 mm depending upon patient needs with a corresponding length ranging from 12 to 20 mm, preferably 16 mm with a width ranging from 10 mm to 14 mm preferably 12 mm, again depending upon surgeon preference and the size of the fusion block which will be used on the individual patient.

Preferably, the load bearing member accounts for about 15% to 40% of the outside exposed area of the implant, preferably around 20%, with a volume of about 10% to about 40% of the implant, preferably around 10% to 20%.

If desired, pins 40 and 42 can be inserted in a through going bores 44 and 46 cut through both component members 12 and 30 to increase stability to the graft. The pins 40 and 42 are preferably constructed of cortical bone but can be constructed from any biocompatible material having the necessary strength requirements including metals, plastics compositions and the like and are friction fit in the respective bores 44 and 46. The cortical front is mated to the cancellous component with the crosspiece inner planar surface being adjacent the cancellous component. The cortical or load bearing component bears not only a compressive load but also serves as an impaction surface. Thus, the surgeon can tap on the anterior cortical surface while impacting the graft without damaging the more brittle cancellous portion of the graft.

Figure 10:
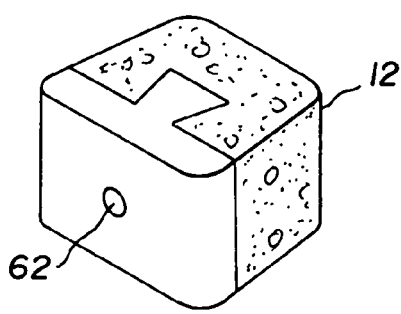
FIG. 10 is a perspective view of an alternative embodiment of the composite cortical and cancellous bone implant with a single throughgoing bore running along the center axis of the dove tail.
Figure 11:
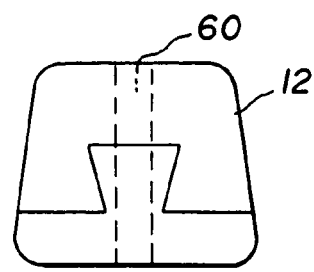
FIG. 11 is a top plan view of the implant of FIG. 10 showing the bore in phantom.

In an alternate embodiment of the invention, a single bore 60 is formed through the center of the dove tail and the base of the U as is seen in FIGS. 10 and 11. A pin 62 is inserted through the axially aligned bores of the cortical load bearing member 30 and the cancellous member 12.

Figure 12:
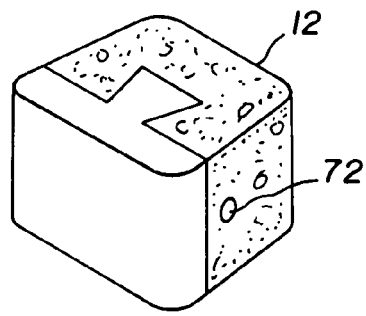
FIG. 12 is a perspective view of an alternative embodiment of the composite cortical and cancellous bone implant with a single throughgoing bore running transverse the axis of the dove tail.
Figure 13:
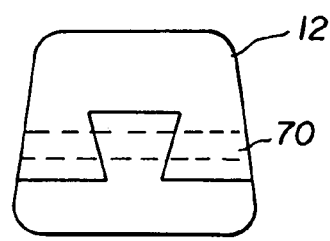
FIG. 13 is a top plan view of the implant of FIG. 12 showing the bore in phantom.

In FIGS. 12 and 13, a bore 70 is cut transverse to the axis of the dove tail shaped stem and across the legs of the cancellous member 12 to receive a pin 72 which provides additional security to the composite implant.

Figure 14:
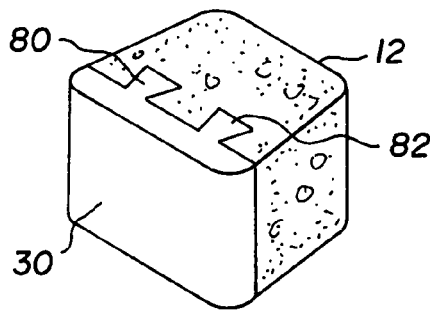
FIG. 14 is a perspective view of an alternate embodiment of the composite cortical and cancellous composite bone implant with multiple dove tails.
Figure 15:
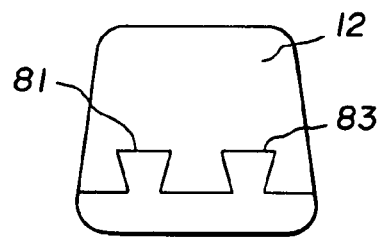
FIG. 15 is a top plan view of the implant of FIG. 14.

In FIGS. 14 and 15, the load bearing member 30 is formed with two dove tail shaped projections 80 and 82 which fit into correspondingly formed recesses 81 and 83, formed in cancellous member 12.

Figure 16:
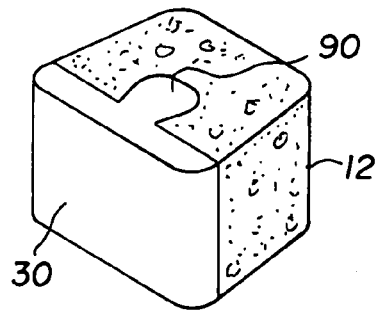
FIG. 16 is a perspective view of an alternative embodiment of the composite cortical and cancellous composite bone implant with a truncated ellipsoid interconnection.
Figure 17:
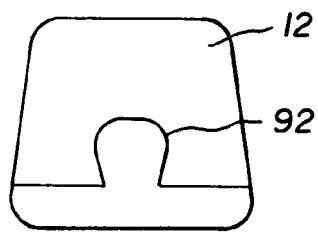
FIG. 17 is a top plan view of the implant of FIG. 16.
Figure 18:
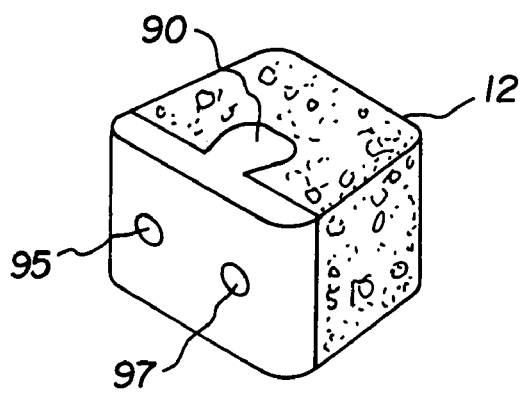
FIG. 18 is a perspective view of the embodiment of FIG. 16 with two angled bores.
Figure 19:
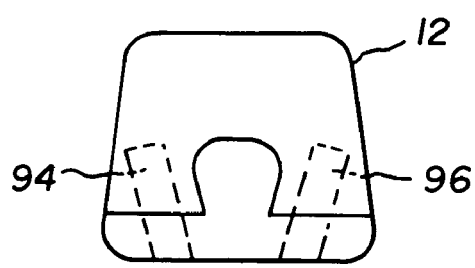
FIG. 19 is a top plan view of the implant of FIG. 18.

In FIGS. 16 and 17, the load bearing member 30 is formed with a bulbous or truncated ellipsoid projection 90 which fits into a similarly configured recess 92 of the cancellous member 12. In FIGS. 18 and 19, the construction of FIG. 16 is shown with two angled bores 94 and 96, cut through the load bearing member 30 and into the cancellous member 12 holding pins 95 and 97.

Figure 20:
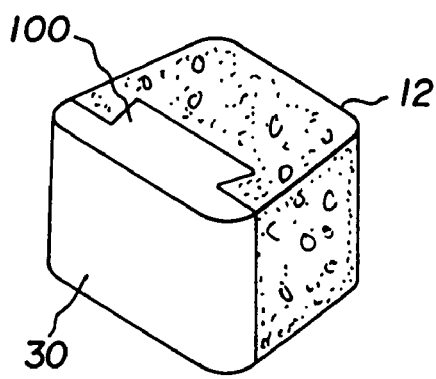
FIG. 20 is a perspective view of an alternate embodiment of the composite cortical and cancellous composite bore implant with a wider dove tail engagement structure.
Figure 21:
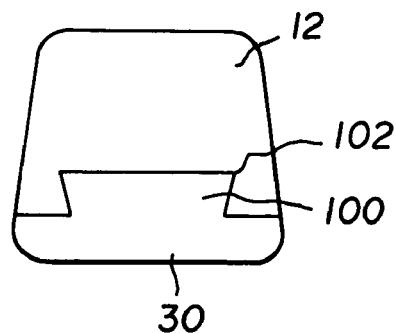
FIG. 21 is a top plan view of the implant of FIG. 20.
Figure 22:
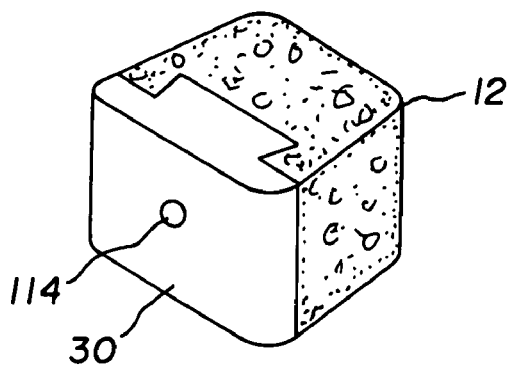
FIG. 22 is a perspective view of the implant of FIG. 20 with a single bore parallel to the center axis of the implant.
Figure 23:
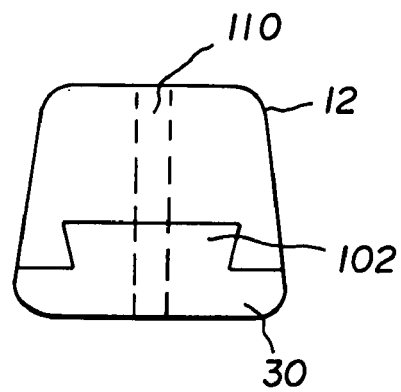
FIG. 23 is a top plan view of the implant of FIG. 22 with the bore shown in phantom.
Figure 24:
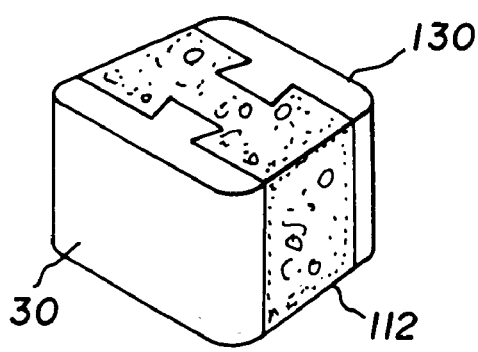
FIG. 24 is a perspective view of an alternate embodiment of the composite cortical and cancellous composite bone implant with load bearing members positioned at both ends.
Figure 25:
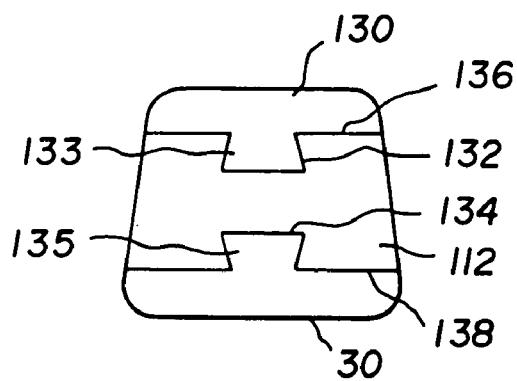
FIG. 25 is a top plan view of the implant of FIG. 20.

Another modification of the invention is shown in FIGS. 20 and 21 in which a widened dove tail mating member 100 extends from the load bearing member 30. This widened dove tail member is at least double the size of the originally shown dove tail member in FIG. 1 and fits into a similarly sized recess 102 in cancellous member 12 as shown in FIG. 21. An added feature to the FIG. 20 embodiment discloses a bore 110 is cut through the load bearing member 30 and centered on the widened dove tail 102. The throughgoing bore 110 holds pin 114.

Figure 26:
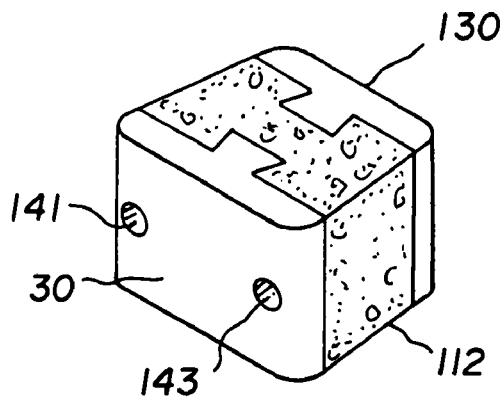
FIG. 26 is a perspective view of the implant of FIG. 24 showing two throughgoing bores.
Figure 27:
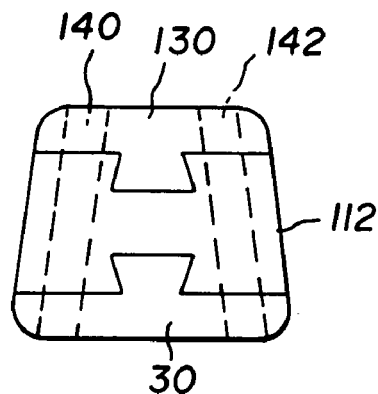
FIG. 27 is a top plan view of the implant of FIG. 26 with the bore shown in phantom.
Figure 28:
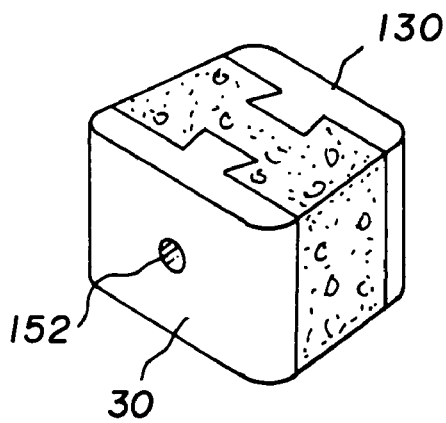
FIG. 28 is a perspective view of the implant of FIG. 24 showing a single throughgoing bore.
Figure 29:
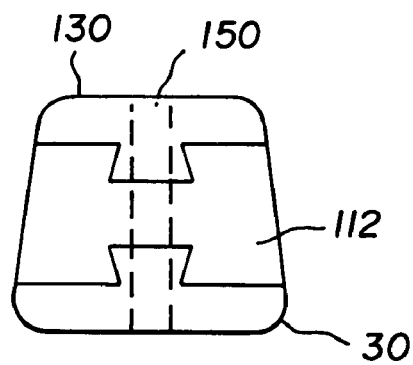
FIG. 29 is a top plan view of the implant of FIG. 28 showing the bore in phantom.

A double sided load bearing implant is shown in FIGS. 24 through 29. In this embodiment, the load bearing members 30 and 130 are mounted on opposite sides of the cancellous member 12 which has corresponding recesses 132 and 134 to hold dove tail projections 133 and 135, The cancellous member 112 is substantially I shaped. Additional component security can be accomplished by providing two throughgoing bores 140 and 142 to hold respective pins 141 and 143, as is shown in FIGS. 26 and 27. A pin variation is shown in FIGS. 28 and 29. This variation uses a single bore 150 running through the center midpoint of the load bearing members 30 and 130 and the central stem of the I shaped member 112. A pin 152 is inserted into the aligned bore 150. It should be noted that all of the embodiments shown in FIGS. 1 through 29, that the sidewalls of the cancellous member are tapered from 100° to 110° and when two facing load bearing members 30 and 130 are utilized that member 130 has a smaller inner flat surface 136 than the flat surface 138 of load bearing member 30 with the respective member 130 having a smaller area size than the load bearing member 30.

While the embodiments shown in FIGS. 1 through 23 have a volumetric ratio in which the load bearing member accounts from 10% to 40% of the mass volume of the composite, the double load bearing embodiment shown in FIGS. 24 through 29 has a higher volumetric mass in that the load bearing surfaces account for about 30% to about 45% of the total volume of the component.

While this operation has been discussed in terms of using the preferred embodiment namely, allograft cortical and cancellous component members of the bone blocks, alternative sources of the components of the components of the bone blocks may be substituted such as xenograft bone or synthetic graft materials. With any of these alternatives, the bone blocks may be shaped as described above. The devices provide the surgeon with a graft that has the combined and best characteristics of both cortical and cancellous bone materials.

The cancellous component can be of partially demineralized or mineralized bone and the load bearing component can be formed of partially surface demineralized or mineralized bone.

The spacers of the present invention were prepared by machining cancellous bone from donors, preferably under 45 years of age which have a denser cancellous structure. Suitable bones which can be used are calcaneus patella, femoral head, long bone condyles and talus. Cortical bone was prepared by machining and was taken from any acceptable donor age. Suitable bones are the radius, ulna, femur, tibia, humerus and the talus.

The unique features of allograft bone that make it desirable as a surgical material are, its ability to slowly resorb and be integrated into the space it occupies while allowing the bodies own healing mechanism to restore the repairing bone to its natural shape and function by a mechanism known in the art as creeping substitution.

It is well known that bone contains osteoinductive elements known as bone morphogenetic proteins (BMP). These BMP's are present within the compound structure of cortical bone and are present at a very low concentrations, e.g. 0.003%. The BMP's are present in higher concentrations in cancellous bone. BMP's direct the differentiation of pluripotential mesenchymal cells into osteoprogenitor cells which form osteoblasts. The ability of freeze dried demineralized bone to facilitate this bone induction principle using BMP present in the bone is well known in the art. However, the amount of BMP varies in the bone depending on the age of the bone donor and the bone processing. Based upon the work of Marshall Urist as shown in U.S. Pat. No. 4,294,753, issued Oct. 13, 1981 the proper demineralization of cortical bone will expose the BMP and present these osteoinductive factors to the surface of the demineralized material rendering it significantly more osteoinductive. The removal of the bone mineral leaves exposed portions of collagen fibers allowing the addition of BMP's and other desirable additives to be introduced to the demineralized outer treated surface of the bone structure and thereby enhances the healing rate of the cortical bone in surgical procedures. In cancellous bone the structure is not as dense as cortical bone exposing the naturally occurring BMP's rendering the entire structure with biological properties similar to full demineralized bone (DBM).

It is also possible to add one or more rhBMP's to the bone by soaking and being able to use a significantly lower concentration of the rare and expensive recombinant human BMP to achieve the same acceleration of biointegration. The addition of other useful treatment agents such as vitamins, hormones, antibiotics, antiviral and other therapeutic agents could also be added to the bone.

Any number of medically useful substances can be incorporated in the cancellous component member or load bearing member by adding the medically useful substances to the same. Such substances include collagen and insoluble collagen derivatives, hydroxyapatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and silver salts. It is also envisioned that amino acids, peptides, vitamins, co-factors for protein synthesis; hormones; endocrine tissue or tissue fragments; synthesizers; enzymes such as collagenase, peptidases, oxidases; polymer cellpl scaffolds with parenchymal cells; angiogenic drugs and polymeric carriers containing such drugs; collagen lattices; biocompatible surface active agents, antigenic agents; cytoskeletal agents; cartilage fragments, living cells and cell elements such red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present as a concentration of $10^5$ and $10^6$ per cc of a carrier, natural extracts, tissue transplants, bioadhesives, transforming growth factor (TGF-beta), insulin-like growth factor (IGF-1); platlet derived growth factor (PDGF), fibroblast growth factor (FGF) (numbers 1-23), osteopontin, vascular endothelial growth factor (VEGF), growth hormones such as somatotropin, cellular attractants and attachment agents, blood elements; natural extracts, tissue transplants, bioadhesives, bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

While the present invention is described for use in the cervical spine, it is also suitable for use in the lumbar and/or thoracic spine. The implant can be provided in a variety of sizes, each size configured to be inserted between a specific pair of adjacent vertebrae. For example, the implant can be provided in selected dimensions to maintain disc height, correct lordosis, kyphosis or other spinal deformities.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What is claimed is:

1. A sterile composite graft compromising:
   a first cancellous bone component member with angled sides and a load bearing component member mounted to said first cancellous bone component member, said load bearing component member has an outside exposed surface area ranging from about 15% to about 40% of the outside exposed surface area of the cancellous member, said load bearing component member is constructed of cortical bone which has surface demineralization, said cancellous bone component member defining a planar engagement surface for the load bearing component member with a shaped recess cut into said planar engagement surface into the interior of the cancellous bone component member with at least a portion of said shaped recess being larger than the opening leading to the shaped recess, said load bearing component member defining an inner planar engagement surface and a locking member extending outward from said engagement surface, said locking member being correspondingly shaped to fit into said shaped recess of said cancellous bone component member holding said first and second component members together in a mated relationship and pin means mounted through said load bearing component member and extending into said cancellous bone component member to prevent sliding movement between said load bearing component member and said cancellous bone component member.

2. A sterile composite graft as claimed in claim 1 wherein said first cancel bus member is constructed of allograft cancellous bone taken from a group of bones consisting of a cancelbous patella, femoral head, long bone condyles and talus.

3. A sterile composite graft as claimed in claim 1 wherein said load bearing component member is cortical bone.

4. A sterile composite graft as claimed in claim 1 wherein said cancellous bone component member has a truncated inwardly inclined cross section.

5. A sterile composite graft as claimed in claim 1 wherein said cancellous bone component is constructed of xenograft cancellous bone.

6. A sterile composite graft as claimed in claim 1 wherein said cancellous bone component member is constructed of allograft bone which is partially demineralized.

7. A sterile composite graft as claimed in claim 1 wherein said locking member has a dove tail configuration and said shaped recess has a corresponding dove tail configuration.

8. A sterile composite graft as claimed in claim 1 wherein at least one of said graft component members includes a cellular material additive taken from a group consisting of red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present as a concentration of $10^5$ and $10^6$ per cc of a carrier.

9. A sterile composite graft as claimed in claim 1 wherein at least one of said graft components include an additive taken from a group of growth factors consisting of transforming growth factor (TGF-beta), insulin-like growth factor (IGF-1); platelet derived growth factor (PDGF), fibroblast growth factor (FGF) (numbers 1-23), osteopontin, vascular endothelial growth factor (VEGF), growth hormones such as somatotropin cellular attractants and attachment agents.

10. A sterile composite graft as claimed in claim 1 wherein at least one of said graft component members include an additive taken from a group of additives consisting of antimicrobials effective against HIV and hepatitis; antimicrobial and/or antibiotics consisting of erythromycin, bacitracin, neomycin, penicillin, polymyxin B, tetracycline, viomycin, chloromycetin and streptomycin, cefazolin, ampicillin, azactam, tobramycin, clindamycin, gentaznycin and silver salts.

11. A sterile composite graft as claimed in claim 1 wherein said pin means comprises a plurality of pins mounted through said load bearing member and seated in blind bores formed in said cancellous member.

12. A sterile composite graft as claimed in claim 11 wherein said plurality of pins are mounted at an angle with respect to the plane of the engagement surface of said load bearing member.

13. A sterile composite graft as claimed in claim 1 wherein said pin means comprise a single pin mounted in a throughgoing bore located in a center axis transverse to the plane of said load bearing member base portion and an axially aligned throughgoing bore of said cancellous member.

14. A sterile composite graft as claimed in claim 1 including a second load bearing member mounted to said cancellous member so that said graft has two load bearing members, one on each end of said cancellous member.

15. A sterile composite graft as claimed in claim 14 wherein each of said load bearing members is of identical configuration.

16. A sterile composite graft as claimed in claim 1 wherein said load bearing member has at least two locking members of the same configuration which extend from the inner engagement surface of said load bearing member and are seated in corresponding formed recesses in said cancellous member.

17. A sterile composite graft as claimed in claim 1 wherein said load bearing member has a substantially T shaped configuration.

18. A sterile composite graft as claimed in claim 1 wherein said cancellous member has a substantially U shaped configuration.

19. A sterile composite graft as claimed in claim 1 wherein said load bearing component has volume measurement which ranges from about 10% to about 40% of the volume measurement of the cancellous member.

20. A sterile composite graft comprising:
a cancellous bone component member and a load bearing component member mounted to said cancellous bone component member, said load bearing component member having an outside exposed surface area ranging from about 15% to about 40% of the outside exposed surface area of the cancellous component member, said cancellous bone component member defining a planar outer surface and defining a shaped recess cut into said planar outer surface extending into the interior of the cancellous bone component member, said load bearing component member having a T shaped configuration with a flat inner surface on the base of the crosspiece and a stem extending outward from said crosspiece flat surface, said stem being configured with a distal portion being larger than its proximal portion to fit into said shaped recess holding said component members together in a mated relationship, said load bearing and cancellous bone component members defining bores which are axially aligned when the component members are mated together and pins mounted in said axially aligned bores, said pins extending across an intersection between said cancellous bone component member and said load bearing component member to prevent sliding movement between said load bearing component member and said cancellous bone component member.

21. A sterile composite graft as claimed in claim 20 wherein said bores are a plurality of bores which are angled with respect to a center axis taken along said stem.

22. A sterile composite graft as claimed in claim 20 wherein said bores extend transverse to a center axis taken along said stem.

23. A sterile composite graft as claimed in claim 20 wherein said bores are angled with respect to a center axis of said stem and end in blind bores in said cancellous member.

24. A sterile composite graft as claimed in claim 20 wherein said crosspiece of said T has a flat distal surface and a flat proximal surface with a curved outer edge section connecting said flat surfaces.

25. A sterile composite graft as claimed in claim 20 wherein said load bearing component stem has a dove tail configuration and is constructed of allograft cortical bone.

26. A sterile composite graft as claimed in claim 20 wherein said cancellous member has a U shaped configuration.

27. A sterile composite graft as claimed in claim 20 wherein said load bearing component has volume measurement which ranges from about 10% to about 40% of the volume measurement of the cancellous member.

28. A sterile composite graft as claimed in claim 20 wherein said load bearing component is constructed of ceramic.

29. A sterile composite graft as claimed in claim 20 wherein said load bearing component is constructed of bioabsorbable polymers.

30. A sterile composite graft as claimed in claim 20 wherein said cancellous bone component is constructed of xenograft cancellous bone.

31. A sterile composite graft as claimed in claim 20 wherein at least one of said graft components include an additive taken from a group of growth factors consisting of transforming growth factor (TGF-beta), insulin-like growth factor (IGF-1); platelet derived growth factor (PDGF), fibroblast growth factor (FGF) (numbers 1-23), osteopontin, vascular endothelial growth factor (VEGF), growth hormones such as somatotropin cellular attractants and attachment agents.

32. A sterile composite graft as claimed in claim 20 wherein at least one of said graft component members includes a cellular material additive taken from a group consisting of red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present as a concentration of $10^5$ and $10^6$ per cc of a carrier.

33. A sterile composite graft comprising:
a cancellous bone component member and cortical bone component member, said cancellous bone component defining a U shaped configuration when viewed from a top planar view with the ends of the legs of the U defining a flat surface and the interior of the U forming a shaped recess, said cortical bone component member having an outside exposed surface area ranging from about 15% to about 40% of the outside exposed surface area of said cancellous bone component member, and defining a flat inner surface which is seated on said cancellous bone component member legs flat surfaces and a mating member extending from said flat inner surface of said bone component member, said mating member being configured to fit into said shaped recess holding a first and second bone components together, said component members each defining bores which are axially aligned when the component members are mated together and pins mounted in said axially aligned bores, said pins extending across an intersection between said cancellous bone component member and said cortical bone component member to prevent relative movement between said load bearing component member and said cancellous bone component member.

34. A sterile composite graft as claimed in claim 33 wherein at least one of said graft components include an additive taken from a group of living cells and cell elements consisting of red blood cells, white blood cells, platelets, blood plasma, pluripotential cells, chondrocytes, bone marrow cells, mesenchymal stem cells, osteoblasts, osteoclasts and fibroblasts, epithelial cells and endothelial cells present in a concentration of $10^5$ and $10^6$ per cc of a carrier.

35. A sterile composite graft as claimed in claim 33 wherein said bores are a plurality of bores which are angled with respect to a center axis of said dove tail mating member.

36. A sterile composite graft as claimed in claim 33 wherein said bores extend transverse to a center axis of said mating member.

37. A sterile composite graft as claimed in claim 33 wherein said bores comprise a plurality of bores which are angled with respect to a center axis of said mating member and end in blind bores in said cancellous member.

38. A sterile composite graft as claimed in claim 33 wherein said mating member has a dove tail configuration and said shaped recess has a corresponding dove tail configuration.

39. A sterile composite graft as claimed in claim 33 wherein said mating member is a truncated ellipsoid and said shaped recess has a corresponding truncated ellipsoid configuration.

40. A sterile composite graft as claimed in claim 33 wherein said load bearing component has a volume measurement which ranges from about 10% to about 40% of the volume measurement of the cancellous member.

41. A sterile composite graft as claimed in claim 33 wherein said cancellous bone component is constructed of xenograft cancellous bone.

42. A sterile composite graft as claimed in claim 33 wherein at least one of said graft components include an additive taken from a group of growth factors consisting of transforming growth factor (TGF-beta), insulin-like growth factor (IGF-1); platelet derived growth factor (PDGF), fibroblast growth factor (FGF) (numbers 1-23), osteopontin, vascular endothelial growth factor (VEGF), growth hormones such as somatotropin cellular attractants and attachment agents.

43. A sterile composite graft comprising:
a first cancellous bone component member with angled sides and a second load bearing component member mounted to said first cancellous bone component member, said load bearing component member has an outside exposed surface area ranging from about 15% to about 40% of the outside exposed surface area of the cancellous member, said cancellous bone component member defining a planar engagement surface for the load bearing component member with a truncated ellipsod shaped recess cut into said planar engagement surface into the interior of the cancellous bone component member with at least a portion of said shaped recess being larger than the opening leading to the shaped recess, said load bearing component member defining an inner planar engagement surface and a locking member extending outward from said engagement surface, said locking member being correspondingly truncated ellipsoid shaped, to fit into said truncated ellipsoid shaped recess of said cancellous bone component member holding said first and second components members together in a mated relationship and pin means mounted through said load bearing component member and extending into said cancellous bone component member to prevent sliding movement between said load bearing component member and said cancellous bone component member.

44. A sterile composite bone graft for use in human implants comprising: an allograft cancellous bone component member and an allograft cortical bone component member mated to the cancellous bone component member, said cancellous bone component member defining a U shaped cross section with end surfaces of the legs of the U forming a flat surface and the interior of the U being formed with a truncated ellipsoid shaped recess and tapered side walls, said cortical bone component member defining a base with an inner surface which seats on said cancellous bone component member flat surface and an ellipsoid shaped mating member extending from said inner surface, said ellipsoid shaped mating member being configured to fit into said ellipsoid shaped recess holding a first and second bone components together.

45. A sterile composite bone graft for use in human implants comprising:
a load bearing member constructed of allograft cortical bone defining a planar surface and a dove tail mating shaped member extending from said planar surface, an allograft cancellous member defining tapered side walls at an angle ranging from about 100° to about 110° from a line drawn through the longitudinal center axis, a flat proximal end surface and a flat distal end surface and a dove tail shaped recess cut into said flat proximal end surface with the narrowest portion of said recess exiting said flat proximal end surface, said allograft load bearing member and allograft cancellous member being mated together, said load bearing member having an outside exposed surface area ranging from about 15% to about 40% of the outside exposed surface area of said load bearing member.

46. A sterile composite graft as claimed in claim 45 wherein said members define bores which are axially aligned when the component members are mated together and a plurality of pins are mounted in said axially aligned bores, said pins extending across an intersection between said cancellous bone number and said load bearing member to prevent sliding movement between said load bearing component member and said cancellous bone component member.

47. A sterile composite graft comprising:
a cancellous bone component member with tapered side walls and two end cortical bone component members mounted to said cancellous bone component member, said cancellous bone component member defining a flat surface on each end with at least one dove tail shaped recess formed in each end surface, each cortical bone component member defining a flat inner surface which seats on said cancellous bone component member end flat surface so that said cortical component members are opposite each other and at least one dove tail shaped mating member extending from said flat inner surface, each dovetail mating member being configured to fit into a corresponding dove tail shaped recess holding said bone components together, said cortical bone component members having an outside exposed surface area ranging from about 30% to about 40% of the outside exposed surface area of the cancellous bone component member, said cortical and cancellous bone component members each defining at least one bore which is axially aligned when the component members are mated together and at least one pin mourned in said axially aligned bores extending across the intersections between said cancellous bone component member and said load bearing component members to prevent relative movement between said load bearing component members and said cancellous bone component member.

* * * * *